(12) United States Patent
Amano et al.

(10) Patent No.: US 11,172,830 B2
(45) Date of Patent: Nov. 16, 2021

(54) OBJECT INFORMATION OBTAINING APPARATUS, DISPLAY APPARATUS, AND DISPLAY METHOD

(71) Applicant: CANON KABUSHIKI KAISHA, Tokyo (JP)

(72) Inventors: Ryosuke Amano, Tokyo (JP); Daisuke Nagao, Kawaguchi (JP)

(73) Assignee: Canon Kabushiki Kaisha, Tokyo (JP)

( * ) Notice: Subject to any disclaimer, the term of this patent is extended or adjusted under 35 U.S.C. 154(b) by 473 days.

(21) Appl. No.: 15/755,969

(22) PCT Filed: Aug. 26, 2016

(86) PCT No.: PCT/JP2016/003896
§ 371 (c)(1),
(2) Date: Feb. 27, 2018

(87) PCT Pub. No.: WO2017/038068
PCT Pub. Date: Mar. 9, 2017

(65) Prior Publication Data
US 2019/0038137 A1  Feb. 7, 2019

(30) Foreign Application Priority Data

Aug. 31, 2015 (JP) .............................. JP2015-170585
May 18, 2016 (JP) .............................. JP2016-099906

(51) Int. Cl.
*A61B 5/095* (2006.01)
*A61B 5/00* (2006.01)
(Continued)

(52) U.S. Cl.
CPC ............ *A61B 5/0095* (2013.01); *A61B 5/743* (2013.01); *G01N 29/0609* (2013.01);
(Continued)

(58) Field of Classification Search
CPC ..... A61B 5/0095; A61B 5/743; A61B 8/4444; G01N 2021/1706; G01N 29/0609; G01N 29/0654; G01N 29/2418; G01N 29/265
See application file for complete search history.

(56) References Cited

U.S. PATENT DOCUMENTS

| 2011/0197679 A1 | 8/2011 | Kono |
| 2015/0148652 A1* | 5/2015 | Wanda ................. A61B 5/0095 600/407 |
| 2015/0369652 A1* | 12/2015 | Sato ....................... A61B 5/748 73/655 |

FOREIGN PATENT DOCUMENTS

| CN | 102843960 A | 12/2012 |
| CN | 103687545 A | 3/2014 |

(Continued)

*Primary Examiner* — Mark D Remaly
(74) *Attorney, Agent, or Firm* — Canon U.S.A., Inc., IP Division

(57) ABSTRACT

An object information obtaining apparatus includes an irradiation unit configured to irradiate the object with measurement light, a probe configured to receive an acoustic wave propagating from the object, a driving unit configured to move the irradiation unit so that a relative position of the irradiation unit with respect to the object is changed, an image capturing unit configured to capture an image of the object and a control unit. The control unit is configured to control a display unit in such a manner that an irradiation position of the measurement light is displayed on the image captured by the image capturing unit.

18 Claims, 11 Drawing Sheets

(51) Int. Cl.
*G01N 29/06* (2006.01)
*G01N 29/24* (2006.01)
*G01N 29/265* (2006.01)
G01N 21/17 (2006.01)
A61B 8/00 (2006.01)

(52) U.S. Cl.
CPC ..... *G01N 29/0654* (2013.01); *G01N 29/2418* (2013.01); *G01N 29/265* (2013.01); *A61B 8/4444* (2013.01); *G01N 2021/1706* (2013.01)

(56) References Cited

FOREIGN PATENT DOCUMENTS

| | | | |
|---|---|---|---|
| JP | 2010201178 | A | 9/2010 |
| JP | 2012137464 | A | 7/2012 |
| JP | 2012179348 | A | 9/2012 |
| JP | 2014-18369 | A | 2/2014 |
| JP | 2014-69032 | A | 4/2014 |
| JP | 2014155638 | A | 8/2014 |
| RU | 2435514 | C1 | 12/2011 |
| WO | 2014013867 | A1 | 1/2014 |

\* cited by examiner

[Fig. 1]
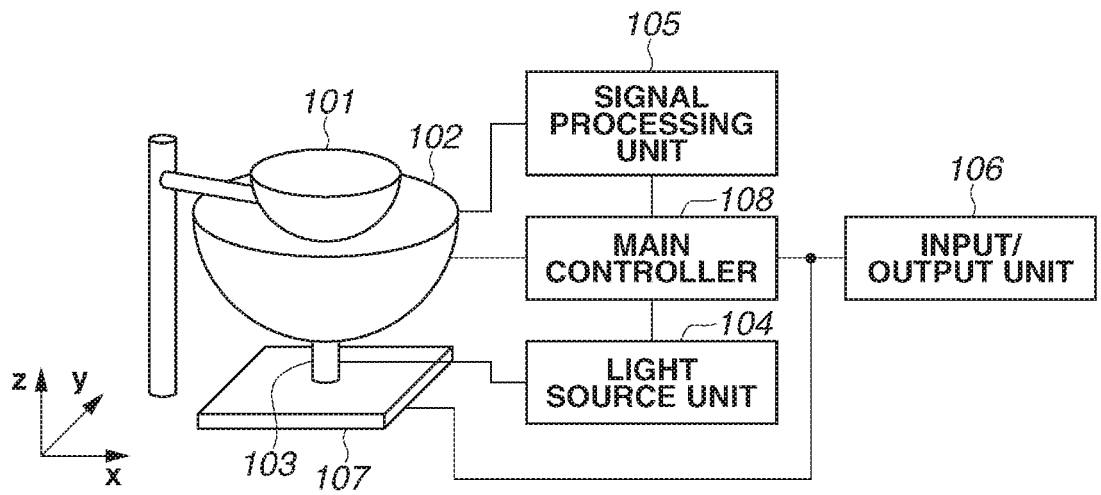
[Fig. 2A]
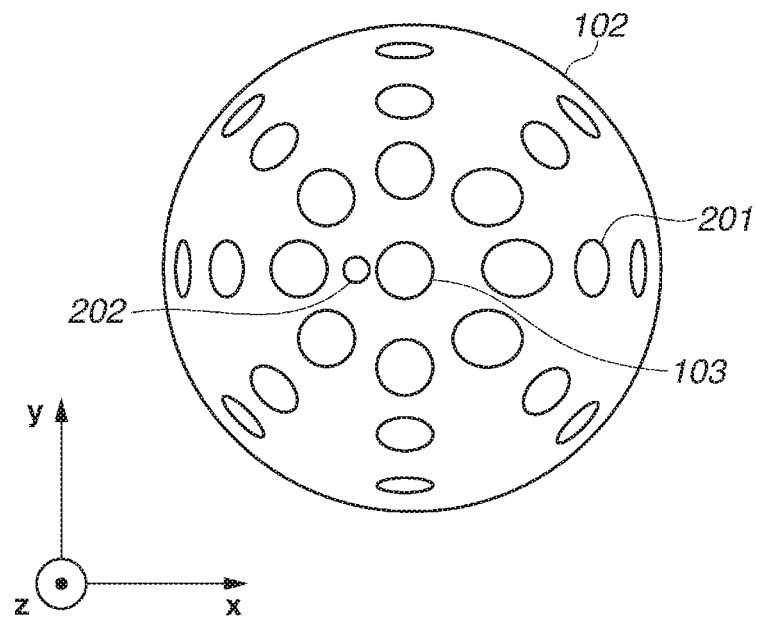

[Fig. 2B]
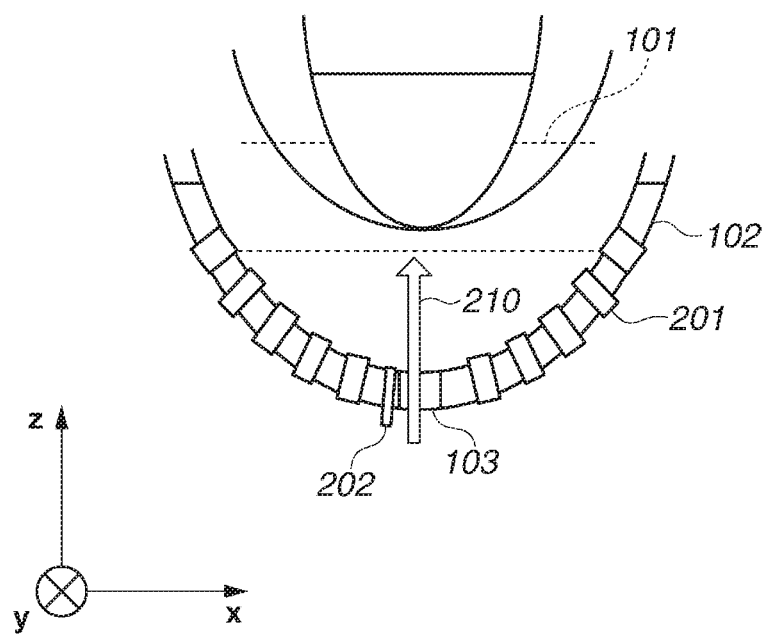

[Fig. 3]
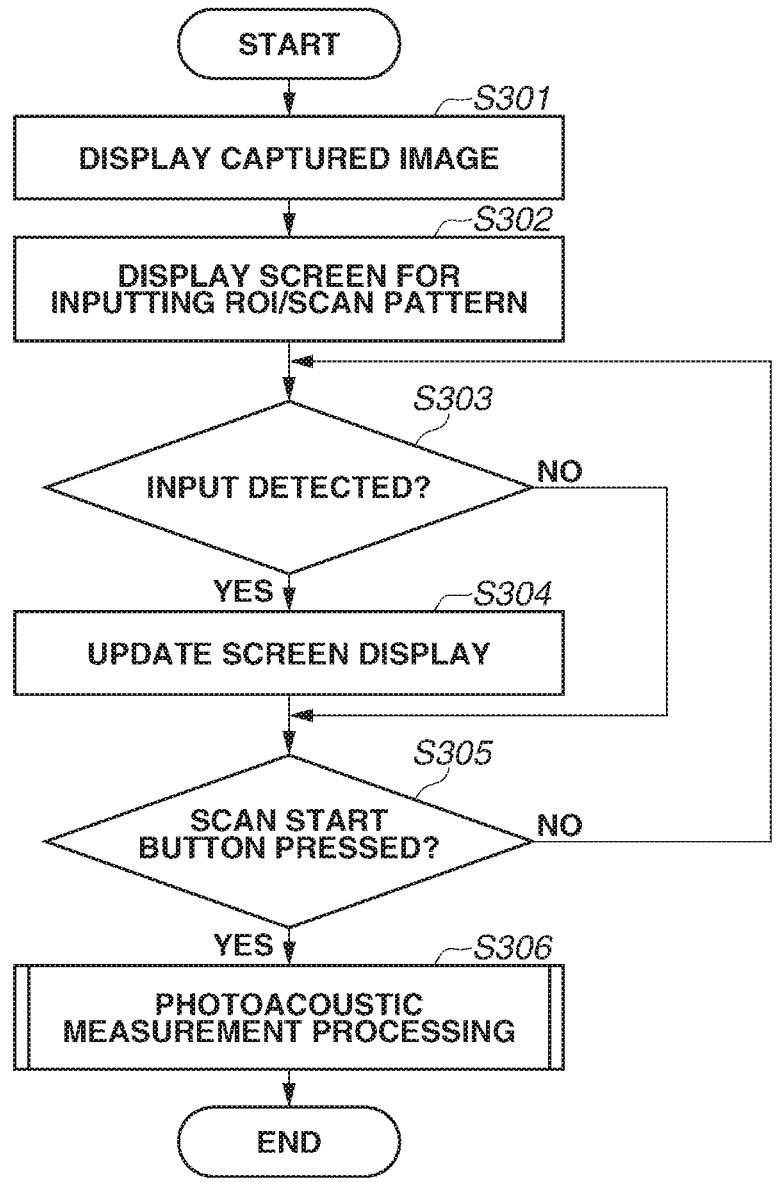

[Fig. 4]
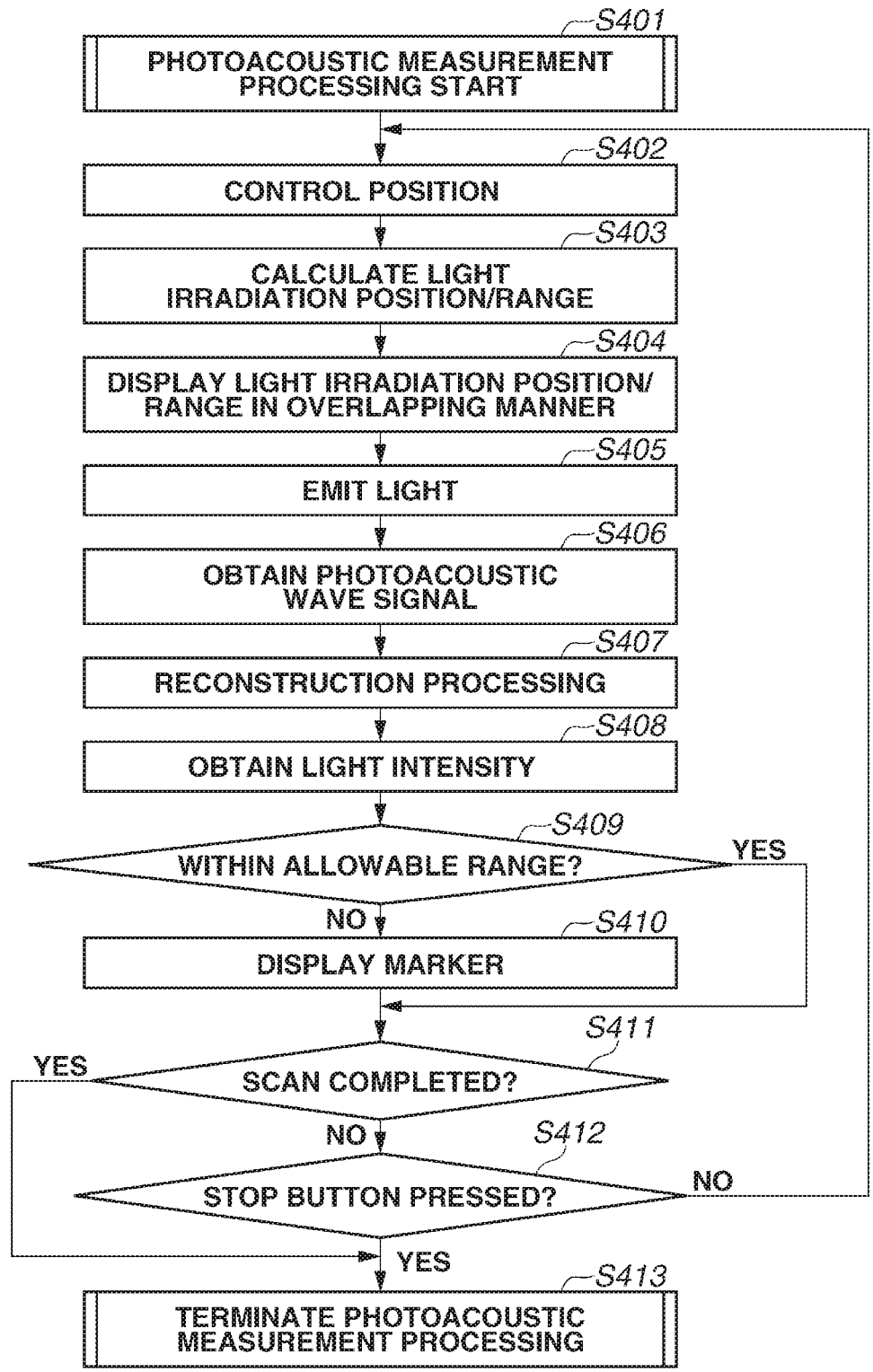

[Fig. 5A]
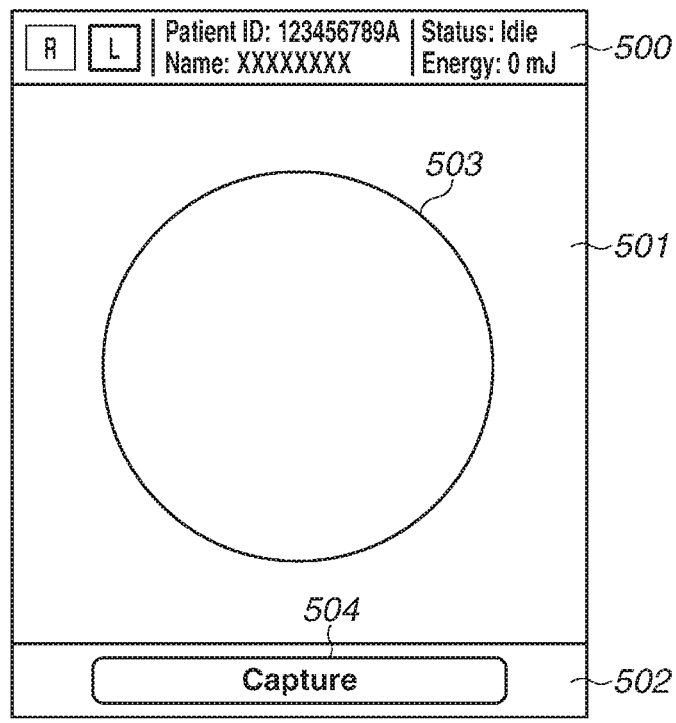
[Fig. 5B]
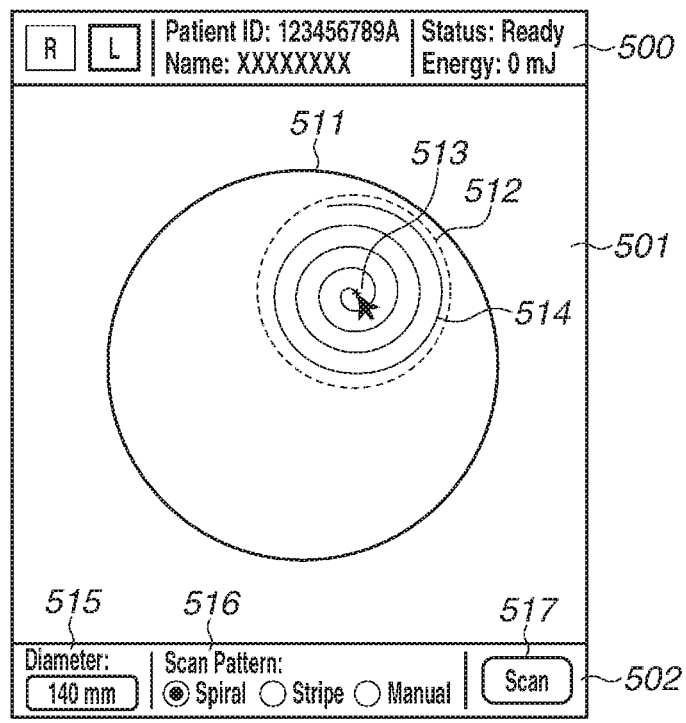

[Fig. 5C]
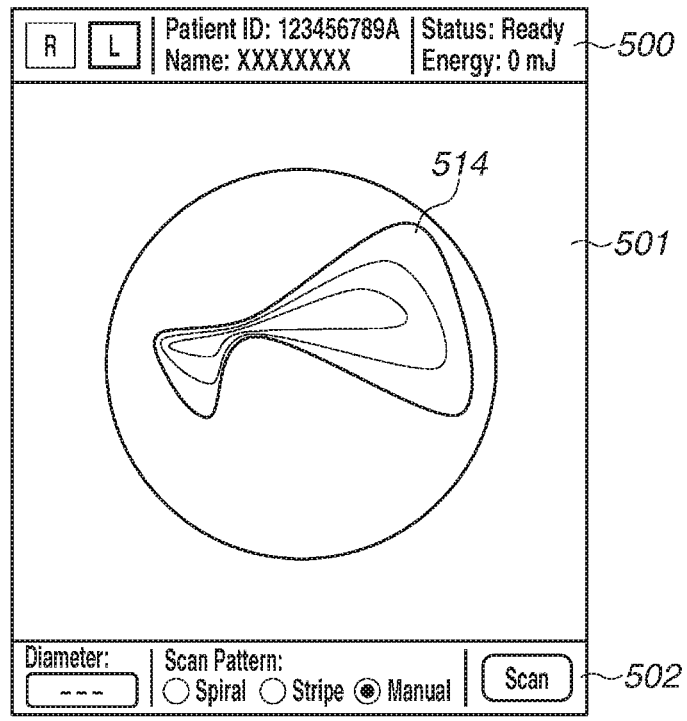
[Fig. 5D]
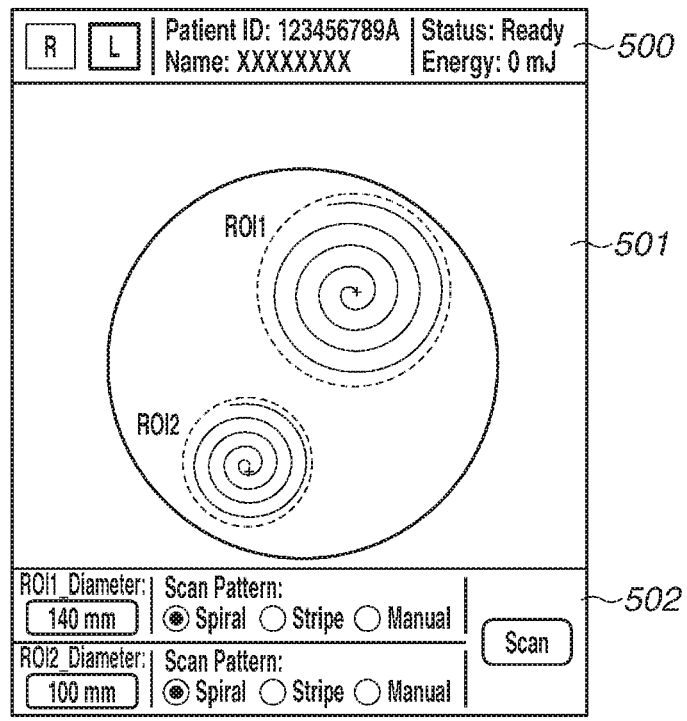

[Fig. 5E]
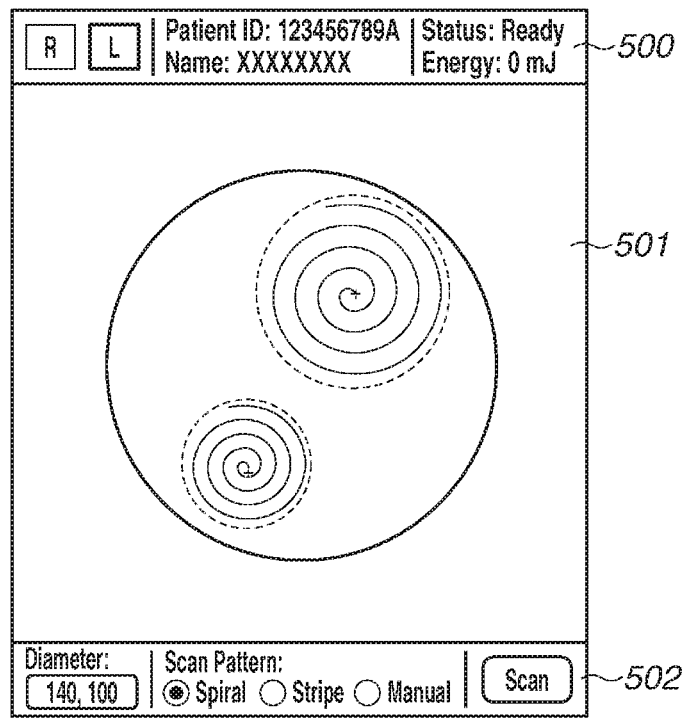
[Fig. 6A]
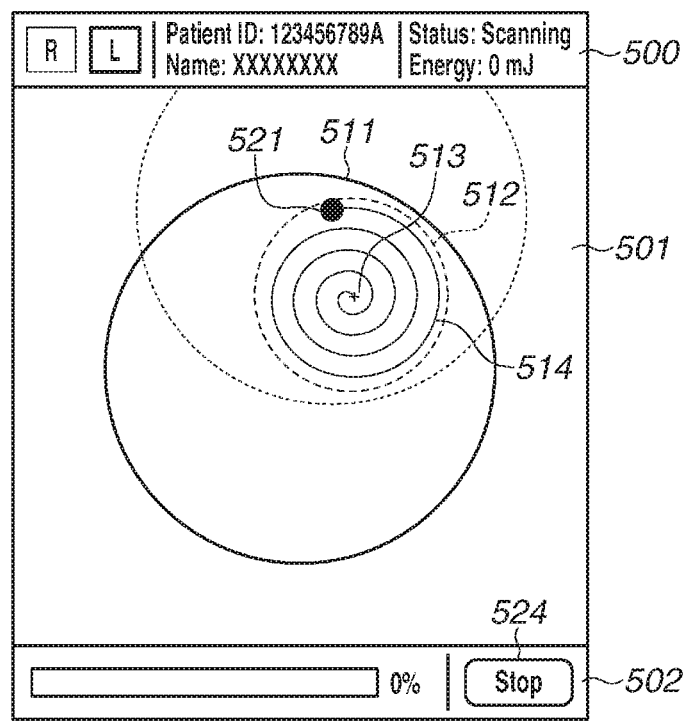

[Fig. 6B]
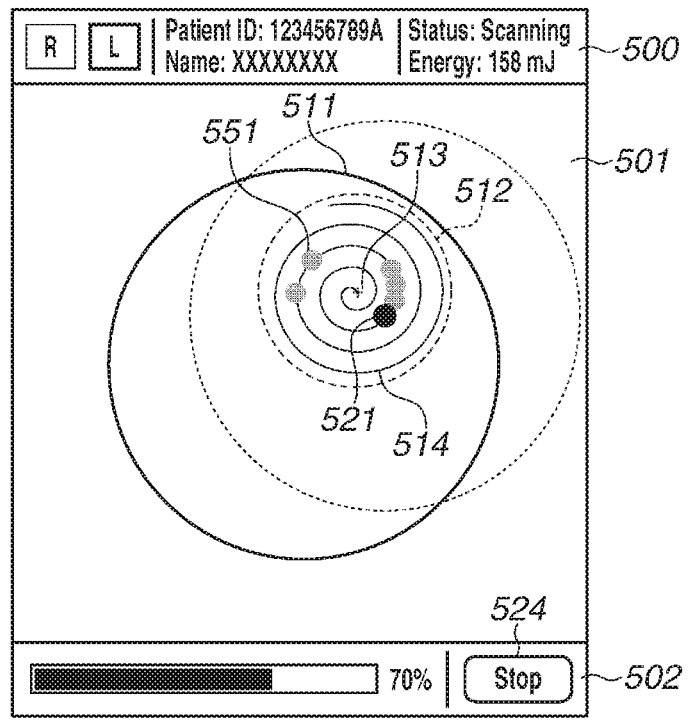
[Fig. 6C]
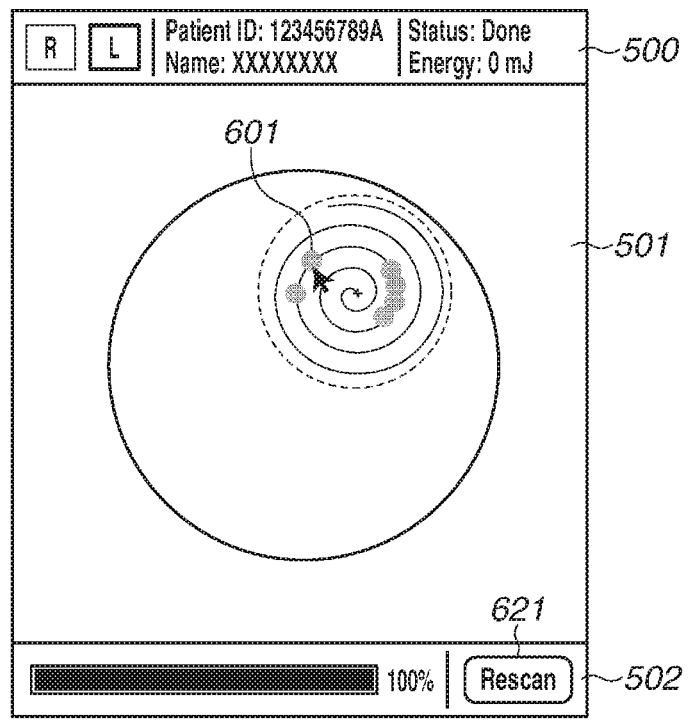

[Fig. 7A]
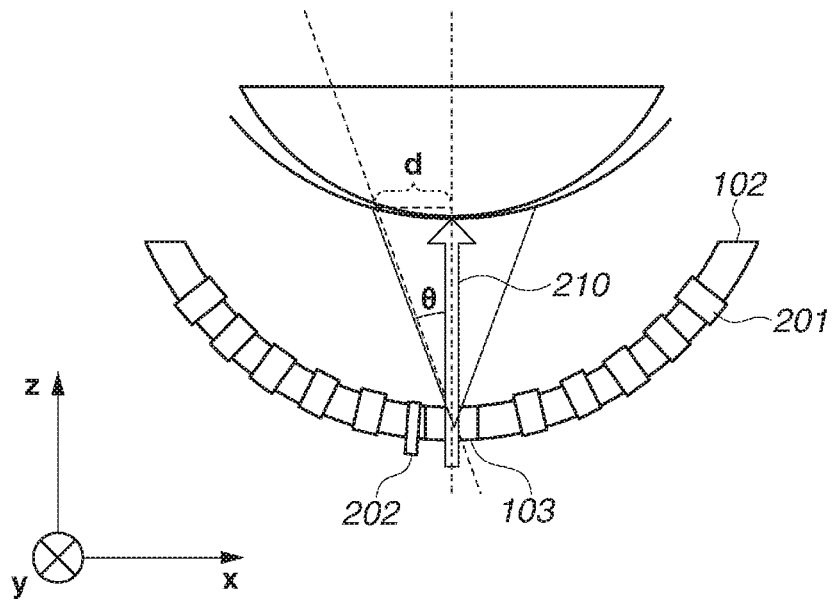
[Fig. 7B]
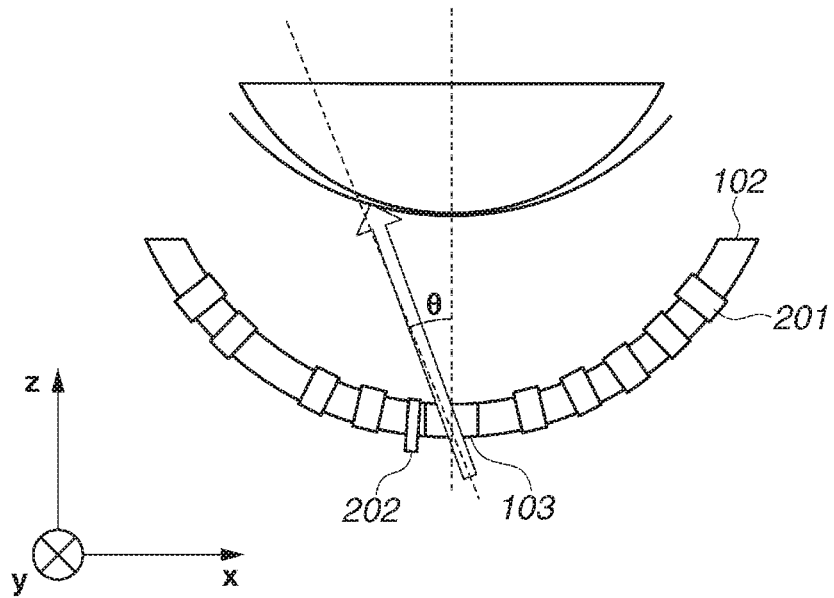

[Fig. 8A]
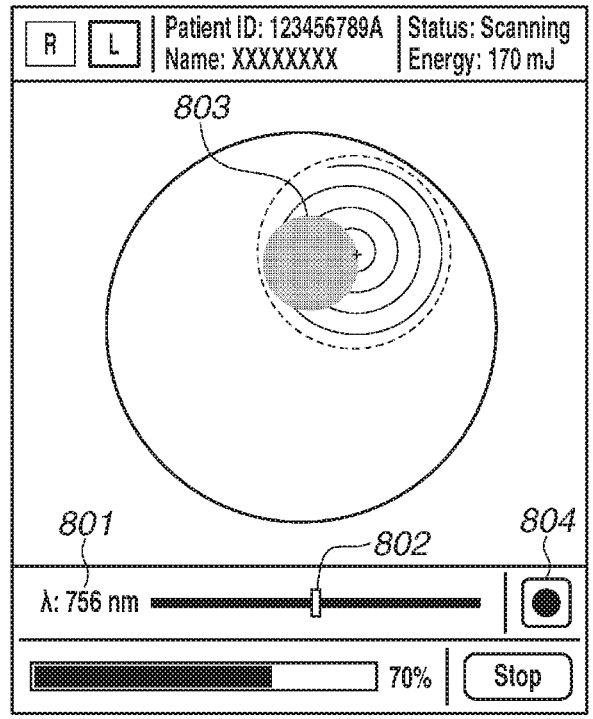
[Fig. 8B]
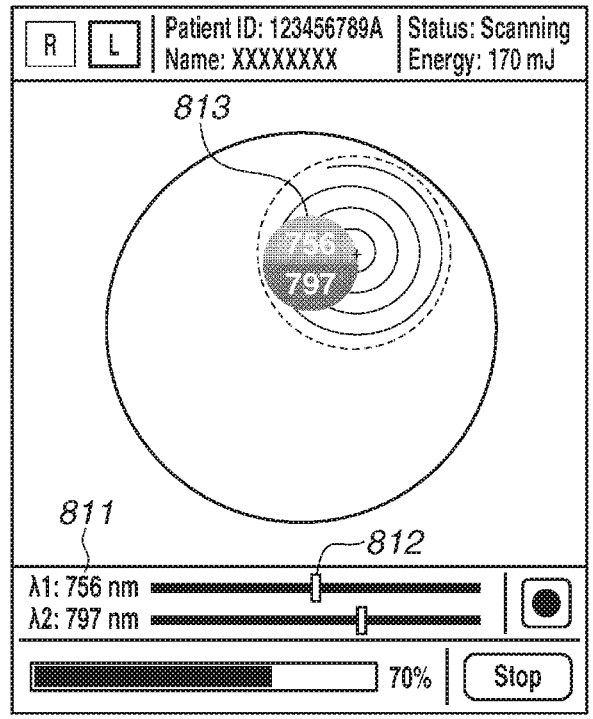

[Fig. 8C]
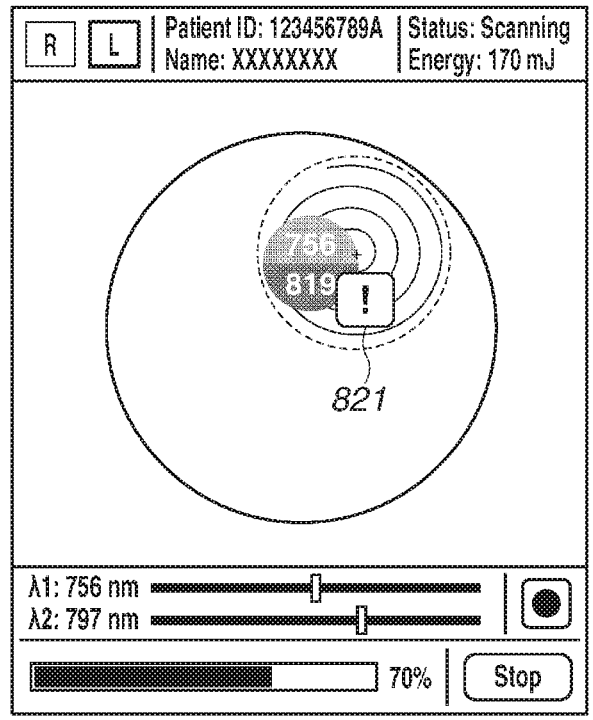
[Fig. 8D]
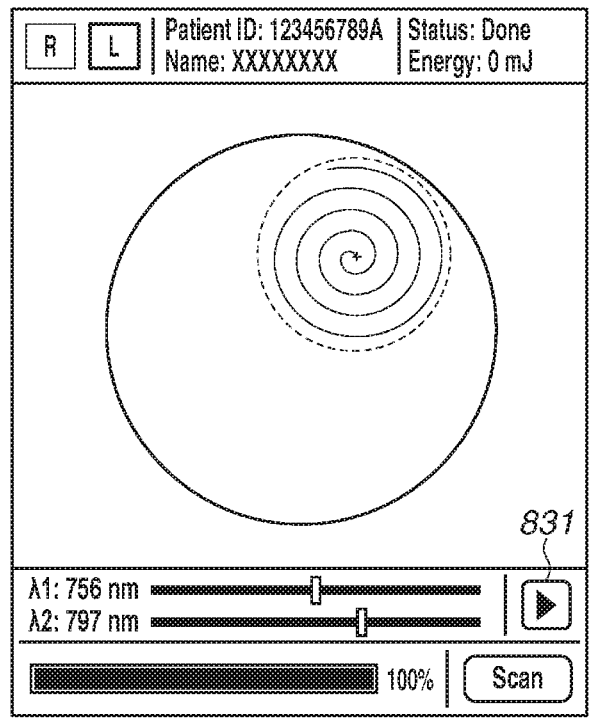

OBJECT INFORMATION OBTAINING APPARATUS, DISPLAY APPARATUS, AND DISPLAY METHOD

TECHNICAL FIELD

The present invention relates to an object information obtaining apparatus, a display apparatus, and a display method for visualizing object information using information about elastic waves propagating from an object.

BACKGROUND ART

There are ongoing studies of photoacoustic apparatuses in the medical field that visualize characteristic information about the interior of an object by receiving and analyzing acoustic waves (hereinafter, also referred to as photoacoustic waves) generated in the object as a result of irradiating the object with light.

Specific examples of the characteristic information about the interior of the object include initial sound pressure of the generated acoustic waves, optical energy absorbance and absorption coefficients obtained from the initial sound pressure, and the concentration of a substance forming a tissue. Examples of the concentration of the object include oxygen saturation, total hemoglobin concentration, and oxyhemoglobin or deoxyhemoglobin concentration.

In the configuration discussed in PTL 1, a plurality of detection elements is disposed on a hemispherical surface, and an acoustic-wave signal is obtained while the relative position of an object and the plurality of detection elements is being changed. In this configuration, the resolution of an obtained image is the highest at and around the center of the hemisphere.

CITATION LIST

Patent Literature

PTL 1: Japanese Patent Application Laid-Open No. 2012-179348

SUMMARY OF INVENTION

Technical Problem

In some cases, an operator wishes to check a light irradiation position on an object surface.

Solution to Problem

To that end, the present invention is directed to an object information obtaining apparatus with which the operator can check an accurate light irradiation position.

An aspect of the present invention for achieving the object is an object information obtaining apparatus including an irradiation unit configured to irradiate an object with measurement light, a probe configured to receive an acoustic wave propagating from the object, a driving unit configured to move the irradiation unit so that a relative position of the irradiation unit with respect to the object is changed, an image capturing unit configured to capture an image of the object and a control unit. The control unit is configured to control a display unit in such a manner that an irradiation position of the measurement light is displayed on the image captured by the image capturing unit.

An aspect of the present invention for achieving the object is a display method including a step of irradiating an object with measurement light, a step of capturing an image of the object, and a step of displaying an irradiation position with the measurement light on the captured image of the object.

Another aspect of the present invention for achieving the object is a display apparatus including an irradiation unit configured to irradiate an object with measurement light, an image capturing unit configured to capture an image of the object, and a control unit. The control unit is configured to control a display unit in such a manner that an irradiation position with the measurement light is displayed on the image captured by the image capturing unit.

Further features of the present invention will become apparent from the following description of exemplary embodiments with reference to the attached drawings.

BRIEF DESCRIPTION OF DRAWINGS

FIG. 1 is a diagram illustrating an example of a configuration of an object information obtaining apparatus.

FIG. 2A is a diagram illustrating an example of a configuration of a supporting member.

FIG. 2B is a diagram illustrating an example of the configuration of the supporting member.

FIG. 3 is a flowchart illustrating an example of a processing flow of object information acquisition processing.

FIG. 4 is a flowchart illustrating an example of photoacoustic measurement processing.

FIG. 5A is a diagram illustrating a display screen.
FIG. 5B is a diagram illustrating a display screen.
FIG. 5C is a diagram illustrating a display screen.
FIG. 5D is a diagram illustrating a display screen.
FIG. 5E is a diagram illustrating a display screen.

FIG. 6A is a diagram illustrating a display screen according to a first exemplary embodiment.
FIG. 6B is a diagram illustrating a display screen according to the first exemplary embodiment.
FIG. 6C is a diagram illustrating a display screen according to the first exemplary embodiment.

FIG. 7A is a schematic diagram illustrating a state where an object is irradiated with light, according to the first exemplary embodiment.
FIG. 7B is a schematic diagram illustrating a state where an object is irradiated with light according to the first exemplary embodiment.

FIG. 8A is a diagram illustrating a display screen according to a fourth exemplary embodiment.
FIG. 8B is a diagram illustrating a display screen according to a fourth exemplary embodiment.
FIG. 8C is a diagram illustrating a display screen according to a fourth exemplary embodiment.
FIG. 8D is a diagram illustrating a display screen according to a fourth exemplary embodiment.

DESCRIPTION OF EMBODIMENTS

Exemplary embodiments of the present invention are described in detail below with reference to the drawings. The same components are denoted with the same reference numerals, and redundant descriptions thereof will be omitted.

A photoacoustic apparatus, which is an object information obtaining apparatus, according to the exemplary embodiments described below can be used, for example, for diagnoses of malignant tumors or vascular diseases, and follow-up of a chemical treatment, for humans and animals. An object can be a part of a living organism, more specifically, a part (e.g., a breast, an organ, a circulatory organ, a digestive organ, a bone, a muscle, and fat) of a human or an animal. Examples of analytes include hemoglobin, glucose, water in the body, melanin, collagen, and lipid. The analytes may be any other substances with a characteristic light absorption spectrum such as a contrast agent, administered to the body, including indocyanine green (ICG).

First Embodiment

<System Configuration>

A configuration of an object information obtaining apparatus according to a first exemplary embodiment is described below with reference to FIG. 1. For the sake of description, an axis in a horizontal direction is referred to as an x axis, an axis orthogonal to the x axis is referred to as a y axis, and an axis orthogonal to the x axis and the y axis is referred to as a z axis.

The object information obtaining apparatus according to the first exemplary embodiment includes an object holding cup 101, a supporting member 102, an input/output unit 106, a main controller 108, a signal processing unit 105, a light source unit 104, a driving unit 107, and a light emission aperture 103.

These components are described below.

The object holding cup 101, serving as a holding unit, is a hemispherical cup made of synthetic resin and used for fixedly holding, and thus immobilizing, an object 100 during measurement. The object holding cup 101 does not necessarily have to hold the entire object 100, and only needs to be capable of holding a portion of the object 100 to be measured. In the description below, the term "object" sometimes refers to a portion of the object to be inspected (an object portion) unless otherwise noted. The object holding cup 101 may be formed of a thin film made of latex rubber or the like, as long as the object can be fixedly held. The object holding cup 101 can be made of a material with high light transmittance, so that pulsed light, serving as measurement light with which the object is irradiated, can be less attenuated. Furthermore, the object holding cup 101 is made of a material allowing a camera 202 (described below) to capture an image of the object portion. Furthermore, the object holding cup 101 is desirably made of a material the acoustic impedance of which is close to that of the object, so that the acoustic waves will be less reflected on the interface between the object and the object holding cup 101. In FIG. 1, the object holding cup 101 is supported by a columnar member. Alternatively, the object holding cup 101 may be held by a bed having an opening in which the object holding cup 101 can be inserted, instead of the columnar member.

The supporting member 102 is a hemispherical casing on which a plurality of transducers 201 and the camera 202 are disposed. In the present exemplary embodiment, the plurality of transducers 201 functions as a probe. To measure the acoustic waves, the supporting member 102 is desirably in a form of a bowl, as illustrated in FIG. 1, filled with an acoustic matching material.

Now, a configuration of the supporting member 102 will be described in detail with reference to FIGS. 2A and 2B. FIG. 2A is a diagram illustrating the supporting member 102 as viewed from a positive to negative direction of the z axis. FIG. 2B is a diagram illustrating the supporting member 102 as viewed from a negative to positive direction of the y axis.

At the bottom of the supporting member 102, the light emission aperture 103 is disposed, and the transducers 201 are disposed in a radial arrangement as illustrated in FIG. 2A. The arrangement is not limited thereto, and for example, the transducers 201 may be in a spiral arrangement with the light emission aperture 103 at the center of the spiral.

The light emission aperture 103 functions as an irradiation unit that irradiates the object with the pulsed light. The light emission aperture 103 outputs the pulsed light, supplied from the light source unit 104, in a direction 210 toward the center of the hemisphere from the bottom of the supporting member 102. An emission angle and a width of the pulsed light are assumed to be fixed in the present exemplary embodiment, but may be changeable. More specifically, the light emission aperture 103 is provided with an optical fiber emission end control actuator to change the emission angle of the pulsed light. The emission end of the light emission aperture 103 is provided with a diaphragm and a diaphragm control actuator for adjusting the diaphragm and the width of the pulsed light can be changed by adjusting the diaphragm using the diaphragm control actuator. In the present exemplary embodiment, a light intensity sensor (not illustrated) is provided with the light emission aperture 103. The light intensity sensor serves as a monitor unit that monitors an energy amount of the pulsed light output from the light emission aperture 103. The monitor unit may also measure the energy amount in an area, on the object portion, irradiated with the pulsed light.

A transducer 201 is an element that converts the acoustic waves propagating from the object into an electric signal. A piezoelectric element or an ultrasound transducer such as a capacitive micromachined ultrasound transducer (CMUT) may be used for the transducer 201. Generally, transducers have directional characteristics to incident angles of the acoustic waves. Thus, each of the transducers 201 is desirably fixed in a direction toward the center of the hemisphere formed by the supporting member 102 so as to be most sensitive. Directional axes of the plurality of transducers 201 do not necessarily intersect at a single point but are desirably concentrated in an area around the center of the hemisphere.

The camera 202 serving as an image capturing unit is directed in a direction toward the center of the hemisphere from the bottom of the supporting member 102, and can capture a still image or a moving image. An imaging element, such as a complementary metal oxide semiconductor (CMOS) sensor and a charge-coupled device (CCD) sensor, may be used for the camera 202. A filter (e.g., a near infrared filter) that reduces the pulsed light entering the camera 202 may be provided. The camera 202 may capture an image of the object portion by using the pulsed light (described below), or may capture an image of the object portion with the object portion irradiated with light other than the pulsed light. The image capturing unit is not limited to the optical imaging unit, and for example, may obtain an outer shape of the object portion from reflected waves of the acoustic waves that is output from the transducers 201. The camera 202 also functions as an irradiation position obtaining unit that obtains information about a position irradiated with light emitted toward the object.

Referring back to FIG. 1, the system configuration is further described below.

One example of the light source unit 104 is a laser that can emit pulsed near infrared light with a wavelength of around 0.7 to 2.5 micrometers. Such a laser typically includes an yttrium aluminum garnet (YAG) laser, an alexandrite laser, and a titanium-sapphire laser but is not limited to these examples. Alternatively, a light source other than the laser, such as a light emitting diode (LED) or a flash lamp, may be used as the light source unit 104. Thus, a light source suitable for each application may be selected as appropriate.

The light source unit 104 and the light emission aperture 103 are connected to each other via an optical fiber and a mirror. The pulsed light is emitted from the bottom of the supporting member 102 in a direction toward the center of the hemisphere.

The signal processing unit 105 is a device that executes signal processing on the electric signal output from the transducers 201, and transmits the resultant signal to the main controller 108. The signal processing unit 105 may perform conversion into a digital signal, amplification, and delay amount control on the electric signal output from the transducers 201. Desirably, for example, the signal processing unit 105 is connected to a light detection sensor attached to the light emission aperture 103, and obtains a signal in synchronization with laser beam emission. For example, the signal processing unit 105 includes an analog amplifier, an analog to digital (AD) converter, and a noise reduction circuit.

The input/output unit 106 receives an operation performed by an operator and notifies the operator of the state of the object information obtaining apparatus. The input/output unit 106 is typically a touch panel display, but may alternatively be a set of independent devices including an input unit, such as a mouse and a keyboard, and a display unit, such as a display. It is only required to provide at least one of a touch panel, mouse, and keyboard as the input unit. The display unit may include a device, other than a touch panel, such as a liquid crystal display and a cathode ray tube (CRT) display that have no touch panel function.

The driving unit 107 is a device that is fixed to the supporting member 102 by using a fixing unit (not illustrated) and moves the supporting member 102 on an xy plane. One example of the driving unit 107 is an electric XY stage in which a stepping motor is installed. The driving unit 107 moves the supporting member 102 to change the relative position of the object and elements, fixed to the supporting member 102, including a pulsed light irradiation unit and the transducers 201. The driving unit 107 may be configured to be capable of moving the supporting member 102 also in a z axis direction.

The main controller 108, serving as a control unit, is connected to each of the light source unit 104, the signal processing unit 105, the input/output unit 106, the driving unit 107, and the camera 202 via an interface such as a universal serial bus (USB). The main controller 108 is a device that controls each of these devices, and is typically a built-in personal computer (PC). The main controller 108 according to the present exemplary embodiment also functions as an irradiation position estimation unit that executes estimation processing for estimating an irradiation position of the pulsed light. The main controller 108 according to the present exemplary embodiment also functions as a reconstruction unit that reconstructs characteristic information about the interior of the object by using a signal received from the signal processing unit 105. As described above, the characteristic information includes a distribution of the initial sound pressure of the photoacoustic waves generated in the object, distributions of optical energy absorbance and absorption coefficients obtained from the initial sound pressure, and a distribution of concentrations of substances forming the tissue, and the like. The main controller 108 performs control in such a manner that the input/output unit displays the reconstructed characteristic information. For example, the main controller 108 can be implemented with a PC. Other examples of a device for implementing the main controller 108 include an application specific integrated circuit (ASIC) and a field programmable gate array (FPGA).

In executing image reconstruction processing, the main controller 108 uses coordinate information about the XY stage obtained when the irradiation unit irradiates the object with the pulsed light. The obtaining of the coordinate information is triggered by a detection signal from the light intensity sensor serving as a light detection unit. The light intensity sensor, however, may output the detection signal when receiving no light, because of electrical noise, such as static electricity. Such erroneous detection leads to obtaining of unnecessary coordinate information by the main controller 108, and should be prevented.

To that end, in the present exemplary embodiment, the main controller 108 obtains the coordinate information about the XY stage when receiving, from the light intensity sensor, a detection signal indicating that incident light with an intensity exceeding a predetermined threshold is received. Then, the main controller 108 again obtains the detection signal from the light intensity sensor and determines whether this detection signal indicates that incident light with an intensity exceeding the predetermined threshold has been received. More specifically, the main controller 108 obtains the coordinate information about the XY stage when determining once that the detection signal indicates reception of incident light with an intensity exceeding the predetermined threshold, and then again determines whether the detection signal indicates the reception of incident light with an intensity exceeding the predetermined threshold. In a case the main controller 108 determines that the intensity of incident light does not exceed the predetermined threshold in the second determination, the main controller 108 invalidates the coordinate information about the XY stage obtained after the first determination. The main controller 108 may perform the invalidation by deleting the coordinate information from a memory provided with the main controller 108, or by providing flag information with which the coordinate information can be identified.

The coordinate information is obtained in a period between the two determinations to reduce a time difference between a timing of emitting the pulsed light and a timing of obtaining the coordinate information. In particular, in a case the photoacoustic measurement is performed while the supporting member 102 is being continuously moved, the supporting member 102 moves during the period between the timing of emitting the pulsed light and the timing of obtaining the coordinate information. This results in a difference between coordinate information at a point when the pulsed light is actually emitted and the obtained coordinate information. This is why obtaining the coordinate information during the period between the two determinations is preferred over obtaining the coordinate information after the two determinations.

An example of a specific method for implementing such determination will be described below. The light intensity sensor is configured to output a detection signal at a low level when incident light with the intensity lower than the predetermined threshold is received by the light intensity sensor, and output a detection signal at a high level for a predetermined period of time when the incident light with the intensity higher than the predetermined threshold is received. A valid detection signal can be distinguished from a detection signal caused by the noise or static electricity, by setting the predetermined period to be a sufficiently long period, for example, about 60 microseconds. Generally, the noise and static electricity is deadened for an extremely short period of time. Thus, when the detection signal is output from the light intensity sensor due to the noise or static electricity, the result of the second determination made by the main controller 108 is different from the result of the first determination. On the other hand, a detection signal, output from the light intensity sensor, generated upon reception of the incident light stays at high level for a sufficiently long period of time, whereby the results are the same between the first and the second determinations. With the two determinations performed as described above, the coordinate information obtained as a result of the erroneous detection due to the noise or static electricity can be invalidated. In this example, the light intensity sensor also serves as the light detection unit. Alternatively, the light detection unit may be provided separately from the light intensity sensor. The information to be obtained, which is the coordinate information on the XY stage in the described case, may be any information with which the relative position of the object and the irradiation unit can be obtained.

<Processing Flow>

Next, processing executed by the object information obtaining apparatus according to the first exemplary embodiment will be described in detail below with reference to FIG. 3 and also to FIGS. 6A, 6B, and 6C. In the following description, the object is a human breast.

FIG. 3 is a flowchart illustrating processing that is executed before the photoacoustic measurement. Here, the processing involves the irradiating of the object with light and the receiving of acoustic waves generated in the object as a result of the light irradiation.

Before the measurement, firstly, the object position is fixed by the object holding cup 101.

In step S301, the main controller 108 displays an image captured by the camera 202 on the input/output unit 106.

FIG. 5A illustrates an example of a screen displayed on the input/output unit 106 at this point. In the present exemplary embodiment, the screen displayed on the input/output unit 106 includes a status notification area 500, an image display area 501, and an operation button display area 502. In FIG. 5A, the status notification area 500, in an upper portion of the screen, indicates whether the object portion is the right or left breast, an identification (ID) and a name unique to the patient with the object portion, a status of the object information obtaining apparatus, and energy of light output from the light emission aperture 103. In the status notification area 500, the sign "R" indicates that the object portion is the right breast, the sign "L" indicates that the object portion is the left breast. In this described case, the left breast is measured, and thus a frame of the sign "L" is highlighted. The sign "R" is on the left side because a doctor facing the patient sees the patient's right breast on the left side. The status of the device is displayed as "Idle" because the measurement is not performed at this point. On the image display area 501, a preview image 503 captured by the camera 202 is displayed. The preview image 503 may be a still image or a moving image. On the operation button display area 502, an operation button is displayed. In FIG. 5A, a capture button 504 is displayed that is pressed for capturing a still image of the object, held by the cup, with the camera 202. In a case the operator selects the capture button 504, a still image of the object held by the cup is captured.

In step S302, the main controller 108 displays, on the input/output unit 106, a screen for prompting the operator to input a region of interest to be subjected to the photoacoustic measurement and a scan pattern for scanning the region of interest.

FIG. 5B illustrates an example of the screen displayed on the input/output unit 106 at that time. In this case, the region of interest has a circular shape and the scan pattern is spiral. A region of interest 512, a center point 513 as the center of the region of interest 512, and a scan pattern 514 are displayed on a still image 511 obtained in step S301. The operation button display area 502 includes an area 515 in which a size of the region of interest is input, an area 516 in which the scan pattern is selected, and an area in which a button 517 for starting the scanning is displayed. In step S303, in response to the operator inputting a numerical value in a text box in the area 515, the main controller updates the size of the region of interest 512 based on the numerical value in step S304. Alternatively, the size of the region of interest 512 may be directly changed by using a mouse, a touch panel, and the like. In such a case, the numerical value in the area 515 indicating the size of the region of interest 512 is updated with the change in the size of the region of interest 512. The position of the region of interest 512 can be moved within the image display area 501 by using the mouse, the touch panel, and the like. In the area 516, options are displayed so that a scan pattern (a spiral or stripe path in this example) set in advance can be selected or a scan pattern can be manually set. As illustrated in FIG. 5C, in a case the operator selects "Manual", the operator can designate a desired scan pattern. More specifically, the operator can draw a desired scan pattern in the image display area 501. The operator may designate a plurality of regions of interest as illustrated in FIGS. 5D and 5E. In such a case, the sizes of the plurality of regions of interest are subsequently input to the area 515. The regions of interest may be labeled as "ROI1" and "ROI2" so as to be identifiable, and the display in the operation button display area may be switched so that the size and the scan pattern of each region of interest can be separately set as illustrated in FIG. 5D. In a configuration where an emission angle or a diameter of the pulsed light from the pulsed light emission aperture 103 is variable, such items can be further set in step S302.

In step S303, the main controller 108 determines whether an input through the input/output unit 106 has been detected. In a case the input is detected (Yes in step S303), the processing proceeds to step S304. In step S304, the main controller 108 updates the display of the screen based on the information thus input. On the other hand, in a case the input has not been detected (No in step S303), the processing proceeds to step S305.

In step S305, the main controller 108 determines whether the scan start button "scan" has been pressed. In a case it is determined that the scan start button "scan" has been pressed (Yes in step S305), the processing proceeds to step S306 where the main controller 108 starts the photoacoustic measurement processing. In a case no region of interest or scan pattern has been designated by the operator (No in step S303), the scanning is performed under a default condition that has been set in advance. On the other hand, in a case the scanning start button "scan" has not been pressed (No in step S305), the processing returns to step S303. The photoacoustic measurement processing is described in detail below.

When the photoacoustic measurement processing in step S306 is completed, the obtaining of the object information is completed.

Next, the photoacoustic measurement processing in step S306 is described in detail.

In step S401, the main controller 108 starts the photoacoustic measurement processing.

In step S402, the main controller 108 moves the supporting member 102 to an initial position determined in accordance with the scan pattern set in step S302. In a case the emission angle or the diameter of the pulsed light from the pulsed light emission aperture 103 has been set in step S302, the initial position is changed based on these settings.

In step S403, the main controller 108 calculates a position on the object to be irradiated with the pulsed light based on the region of interest (range targeted for photoacoustic measurement), the scan pattern set in step 302, and the emission angle and the diameter of the pulsed light, and the like.

A method for calculating a light irradiation position and range is described below with reference to FIGS. 7A and 7B. Here, the light emitted onto the object is assumed to form a circular shape. The light irradiation position corresponds to the center of the circle and the light irradiation range is described using the radius of the circle.

FIGS. 7A and 7B are schematic cross-sectional views illustrating a state where the object is irradiated with the pulsed light as viewed in a negative to positive direction on the y axis.

FIG. 7A is a schematic view illustrating a case where the emission angle of the pulsed light is set so that an emission direction of the pulsed light is parallel with the z axis. Here, the x and y coordinates are the same between the center point of the light irradiation position and the center coordinates of the pulsed light emission aperture 103.

In a case the light irradiation range on the object is unknown, the light irradiation range, on the object, centered on each irradiation position can be calculated from the emission angle of the pulsed light, a vertex angle 20 of the pulsed light with the pulsed light emission aperture 103 as the vertex, the surface shape of the object, and the like. The surface of the object can be nearly shaped into the shape of the object holding cup 101. In the example in FIG. 7A, the x and y coordinates are the same between the center point of the light irradiation position and the center of the pulsed light emission aperture 103. A radius d of the light irradiation range can be calculated by obtaining coordinates ($x_i$, $y_i$, $z_i$) at the intersection of a straight line that passes through the center coordinates ($x_c$, $y_c$, $z_c$) of the pulsed light emission aperture 103 and is inclined by an angle $\theta$ with respect to the z axis with a contour of the object holding cup 101. The pulsed light irradiation range centered on each light irradiation position may be calculated in advance and the calculated result is stored in a memory or the like.

FIG. 7B is a schematic view illustrating a case where the emission angle of the pulsed light is an angle $\theta$ with respect to the z axis. In this case, when the light irradiation range centered on each irradiation position is unknown, the light irradiation range can be calculated. A distance sensor (such as an ultrasound distance sensor or an infrared distance sensor) is installed in the object holding cup 101 or the supporting member 102 and measure the positional coordinates at each point on the contour of the object. The pulsed light irradiation position on the object has the same coordinates as that of the intersection of the straight line that passes through the center coordinates of the pulsed light emission aperture 103 and is inclined by the angle $\theta$ with respect to the z axis with the contour of the object holding cup 101. In a case the laser beam is diffused light, the calculation method described above with reference to FIG. 7A is used in combination with the calculation in this case. The light emitted onto the object may not form a circular shape, and the light irradiation range in such a case may be calculated by using ray tracing. The pulsed light irradiation range centered on each light irradiation position may be calculated in advance and the calculated result may be stored in the memory and the like, also in a case the emission direction of the pulsed light is not in parallel with the z axis. The light irradiation position calculated here is not necessarily represented by absolute coordinates, and may be in any form as long as the position on the object to be irradiated with light can be roughly calculated. For example, in a case the area of the object portion is divided into a plurality of areas, calculation may be made to determine which one of the plurality of areas is an irradiation area.

The flowchart in FIG. 4 is further described.

In step S404, the main controller 108 displays the light irradiation position and range, based on the coordinates of the pulsed light irradiation position calculated in step S403, on the still image 511 in an overlapping manner. Here, the positions of the supporting member 102 and of the light emission aperture 103 may also be displayed on the still image 511 in an overlapping manner. An area to be irradiated with pulsed light may be displayed in addition to or instead of the pulsed light irradiation position. Furthermore, not only the latest irradiation position but also a path of the irradiation position or a path of estimated position corresponding to the next irradiation position and after may be displayed as the pulsed light irradiation position. FIG. 6A illustrates an example of a display immediately after the photoacoustic measurement has started. A marker 521 indicating a light irradiation position represents the light irradiation area calculated, based on the shape or the size, in step S403. On this screen, a stop button 524, for issuing an instruction to stop the measurement, and a status bar, indicating the progress of the measurement, are displayed on the operation button display area 502. For example, the operator can stop the measurement in a case the patient moves while the measurement is in process, or in a case it is displayed that a position deviated from the scan path set in step S302 is to be irradiated with light. The main controller 108 may forcibly terminate or temporarily stop the measurement processing automatically in a case a position deviated by a predetermined amount or more from the scan path set in step S302 is to be irradiated with the light.

One example of a method for evaluating an amount of the deviation from the scan path is based on determination using a distance between light irradiation positions. More specifically, it is determined that the irradiation position has deviated from the scan path set in step S302 by a predetermined amount or more in a case, for example, a distance between the center positions of the light irradiation ranges, each centered on a different one of adjacent light irradiation positions, is larger than a predetermined threshold. The threshold may be a constant value, or may be a value determined based on the irradiation range calculated in step S403. The threshold may be settable by the user. Furthermore, It may be determined that the deviation amount is equal to or larger than the predetermined amount in a case the distance between the irradiation position calculated in step S403 and the irradiation position set in step S302 is larger than a larger one of the radii of the irradiation range calculated in step S403 and the irradiation range set in step S302.

The amount of deviation from the scan path may be determined based on the size of the light irradiation range. More specifically, it may be determined that the amount of deviation is equal to or larger than the predetermined amount in a case a difference between the irradiation range calculated in step S403 and the irradiation range set in step S302 in size is larger than a threshold. For example, it is determined that the amount of deviation is equal to or larger than the predetermined amount in a case one of the ranges is 1.5 or greater times larger than the other.

Determination with a higher accuracy can be achieved by using the plurality of determination methods described above in combination.

Furthermore, the main controller 108 may count how many times the irradiation position calculated in step S403 has deviated from the irradiation position set in step S302 by a predetermined amount or more, and terminate the photoacoustic measurement in a case the counted number of times exceeds a threshold. This determination may be made on the basis of the irradiation range instead of the irradiation position.

The threshold used for determining how many times the deviation has exceeded the threshold may be set by using the number of acoustic-wave signals used for constructing each voxel in a reconstructed image. For example, an accuracy of a voxel value calculated with a small number of photoacoustic signals is low. Thus, a lower limit value may be set for the number of photoacoustic signals used for calculating the voxel value. The main controller 108 may forcibly terminate the measurement upon determining that the obtainable number of photoacoustic signals falls below the lower limit value as a result of the amount of deviation of the irradiation position having exceeded the threshold.

In step S405, the main controller 108 irradiates the object with the pulsed light. In step S406, the main controller obtains a photoacoustic wave signal.

In step S407, the main controller executes reconstruction processing for visualizing information about the interior of the object by using the acoustic waves received in step S406.

In step S408, the main controller 108 acquires an intensity of the pulsed light with the light intensity sensor installed in the pulsed light emission aperture 103.

In step S409, the main controller determines whether the intensity acquired in step S408 is within an allowable range determined based on upper and lower limit values set in advance. When the intensity of the pulsed light is out of the predetermined allowable range (No in step S 409), the processing proceeds to step S410. In step S410, the main controller 108 displays information indicating that the intensity has exceeded the upper limit value or has fallen below the lower limit value to the operator. FIG. 6B illustrates an example of a screen where a marker 551 is at a position, on the screen, corresponding to the irradiation position, on the object, at which the pulsed light has been emitted with the intensity out of the allowable range. The color of the marker 551 may be changed in accordance with the intensity of the corresponding irradiation position. A popup window, color change, or the like may be used for the notification instead of the marker 551. In the present exemplary embodiment, in a case the intensity of the pulsed light is out of the predetermined range, the measurement processing continues with the marker 551 being displayed in the overlapping manner. Alternatively, the main controller 108 may temporarily stop or terminate measurement processing forcibly in a case the pulsed light with the intensity out of the predetermined range is emitted. Furthermore, the processing to be executed next may be different between the case where the intensity has exceeded the upper limit value of the predetermined range and the case where the intensity has fallen below the lower limit value of the predetermined range. For example, in a case the intensity has exceeded the upper limit value, the processing may be stopped to prevent the patient's body from being adversely affected, and in a case the intensity has fallen below the lower limit value, the operator may determine whether to continue or stop the measurement processing. At least one of the size, the shape, and the color of the marker to be displayed on the screen may be different between the case where the intensity has exceeded the upper limit value and the case where the intensity has fallen below the lower limit value. In such a manner, the operator can recognize whether the intensity of the pulsed light has exceeded or fallen below the predetermined range.

A way to notify the operator of the intensity of the pulsed light out of the predetermined range is not limited to display of a maker. Alternatively, a display mode of an image may be changed. For example, in a case the intensity of the pulsed light is out of the predetermined range, the brightness of the irradiation position on the still image may be changed in a blinking manner, or the irradiation position is displayed with a color different from its periphery.

The main controller 108 may count the number of times the pulsed light, with the intensity out of the predetermined allowable range, has been emitted, and forcibly terminate the measurement processing in a case the number of times thus counted exceeds a threshold. For example, a threshold may be set for each of the number of times the intensity of the pulsed light has exceeded the upper limit value of the allowable range and the number of times the intensity has fallen below the lower limit value, and the main controller 108 terminates the measurement processing in a case the threshold is exceeded. In this case, the threshold for the number of times the pulsed light intensity has exceeded the upper limit value of the allowable range is desirably smaller than that for the number of times the pulsed light intensity has fallen below the lower limit value. This is because the number of Limes the intensity of the pulsed light exceeds the upper limit of the allowable range should be small. In one specific example of the processing, the main controller 108 immediately terminates the measurement upon determining that the intensity of the irradiated pulsed light has exceeded the upper limit value of the allowable range, and continues the measurement in a case the intensity has fallen below the lower limit value as long as the counted value does not exceed the threshold.

In a case the main controller 108 determines that the intensity of the pulsed light is within the predetermined range (Yes in step S409) or after the main controller 108 displays the marker in step S410, the processing proceeds to step S411. In step S411, the main controller 108 determines whether the measurement has been completed for all of the light irradiation positions in the region of interest set in step S302. In a case the main controller 108 determines that the measurement has been completed (Yes in step S411), the processing proceeds to step S413 where the main controller 108 terminates the measurement. On the other hand, in a case the main controller 108 determines that the measurement has not been completed (No in step S411), the processing proceeds to step S412.

In step S412, the main controller 108 determines whether the stop button 524 has been pressed by the operator. In a case the stop button has not been pressed (No in step S412), the processing returns to step S402.

The processing for determining whether the stop button 524 has been pressed is not limited to the timing after step S411, and may be executed during any preceding processing step in an event driven manner. More specifically, in a case the stop button 524 is pressed during a processing step before step S411, the operation in the processing step may be immediately stopped, and the processing may proceed to step S413 where the photoacoustic measurement processing is terminated.

The position irradiated with the pulsed light with an intensity out of the predetermined range may be measured again after the photoacoustic measurement processing is terminated in step S413. More specifically, in a case the operator designates a marker 601 and presses a rescan button 621 as illustrated in FIG. 6C, the main controller 108 executes remeasurement (processing in steps S401 to S410) for only the position corresponding to the designated marker 601, and then terminates the measurement processing. In the remeasurement, the pulsed light emission aperture 103 may be moved in a scan pattern different from that in the first measurement. For example, the main controller 108 may calculate the shortest path passing through the position of the marker as the remeasurement target, and the remeasurement may be performed along the path.

The number of photoacoustic signals may be compensated by performing processing for emitting the pulsed light within the measurement range and receiving the acoustic waves, for the number of times the pulsed light with the intensity out of the allowable range has been emitted. For example, in a case the spiral scan pattern as illustrated in FIG. 5B is employed, the spiral path may be extended, and the processing for emitting the pulsed light and receiving the acoustic waves may be executed on the extended path.

In a case the deviation amount of the light irradiation position or range or the pulsed light intensity is repeatedly out of the allowable range during the photoacoustic measurement processing, the main controller 108 may issue a notification for prompting the user to adjust the device to correct the amount of deviation or the intensity. The notification may be issued by displaying a message on the input/output unit 106 or through voice. Alternatively, the photoacoustic device may automatically correct them. For example, in a case the amount of deviation of the light irradiation position or range is continuously at a certain level or more, an XY vector with a value offsetting the deviation may be set as an offset for the coordinate position of the XY stage of the driving unit 107. In a case the difference between the light irradiation ranges is continuously at a certain level or more, the emission angle and the diameter of the pulsed light may be reset. In a case the pulsed light intensity is continuously out of the allowable range, the setting value of the amount of light may be adjusted by using an offset with a value offsetting the excess amount.

In a case the operator presses the rescan button 621 after stopping the measurement processing that had been in process by pressing the stop button 524, the measurement processing may be resumed from the point where the preceding processing has stopped. In a case the measurement is stopped, a marker indicating the last irradiation position before the measurement is stopped may be displayed. Furthermore, a marker indicating the first irradiation position in the rescanning may be displayed.

The processing in step S407 does not necessarily need to be executed between steps S406 and S408, and may be executed in parallel with the processing in step S408 and after, or may be executed after step S413. A favorable image can be obtained through reconstruction processing based on the acoustic waves not including acoustic waves obtained from the pulsed light irradiation for which the amount of deviation of the light irradiation position or range is determined to be the predetermined level or more. Furthermore, the reconstruction processing may be executed based on acoustic waves not including acoustic waves obtained when the pulsed light has not been emitted toward the object. A favorable image can be also obtained through reconstruction processing based on acoustic waves not including acoustic waves obtained from a position determined to have been irradiated with pulsed light with an intensity out of the predetermined range. A favorable image can be obtained through reconstruction processing based on positions where the acoustic waves have been generated, on the basis of the light irradiation position or the light irradiation range calculated in step S403.

In the present exemplary embodiment described above, the light irradiation position is displayed as an image in step S404, and then the light irradiation in step S405 is performed. Alternatively, the processing in steps S403 and S404 may be executed in parallel with the processing in step S405, as long as the processing in steps S404 and S405 is completed before step S412.

As described above, in the present exemplary embodiment, an operator can check an irradiation position of the pulsed light while photoacoustic measurement is in process, by displaying the irradiation position of the pulsed light on an object image.

The operator can check a measurement range and a scan pattern before the measurement starts, by displaying, on the object image, the scan pattern related to light irradiation for a region of interest designated by the operator on the object image.

Second Exemplary Embodiment

A second exemplary embodiment of the present invention will be described below, by focusing mainly on a difference from the first exemplary embodiment.

An object information obtaining apparatus according to the present exemplary embodiment includes a reference light irradiation unit (not illustrated). The object information obtaining apparatus irradiates an object with reference light, captures an image of the object in a state of being irradiated with the reference light, and displays pulsed light irradiation position on the image.

<System Configuration>

In the present exemplary embodiment, the reference light can be emitted along the same light path as the pulsed light used for obtaining the object information, with a light source unit for the reference light added to the pulsed light emission aperture 103. Here, the pulsed light emission aperture 103 also serves as the reference light irradiation unit. The reference light can be emitted along the same light path as the pulsed light used for obtaining the object information, also by using the light source unit 104 as a light source unit. The light source unit 104 can supply the reference light, different from the pulsed light used for obtaining the object information, to the pulsed light emission aperture 103. The reference light may be visible light or any light, other than the visible light, with a wavelength in a range that can be detected by the camera 202. The reference light may be emitted onto the object along a light path different from that of the pulsed light, as long as the reference light and the pulsed light can be emitted at the same position on the object. Here, the pulsed light and the reference light with their irradiation areas at least partially overlapping each other are recognized as being emitted on the same position.

<Processing Flow>

A processing flow according to the present exemplary embodiment is similar to that illustrated in FIG. 3, but has step S306, where the photoacoustic measurement processing is executed, different from that in the first exemplary embodiment. More specifically, in the present exemplary embodiment, estimation of the pulsed light irradiation position, displaying of a marker on the image, and the like are not required. Thus, steps S403, S404, S409, and S410 are omitted from the flow illustrated in FIG. 4. The present exemplary embodiment is further different from the first exemplary embodiment in that not only the pulsed light but also the reference light is emitted in step S405. The reference light is emitted before the pulsed light is emitted, whereby unnecessary pulsed light that would be emitted on a position deviated from a set irradiation position can be prevented from being emitted.

In a case the photoacoustic measurement according to this flow is performed while the pulsed light is continuously emitted, the reference light and the pulsed light are alternately emitted while the supporting member 102 is moving. In the present exemplary embodiment, the reference light and the pulsed light are emitted at the same position. Alternatively, the reference light and the pulsed light may be emitted at different positions while the supporting member 102 is continuously moving, so that noise produced by switching the driving unit 107 between operating and stopped states can be reduced. In such a case, the irradiation position of the reference light may be set to be close to an actual irradiation position of the pulsed light by, for example, adjusting the emission angle and the diameter of the reference light emitted from the pulsed light emission aperture 103.

Alternatively, the reference light and the pulsed light may be simultaneously emitted. In such a case, visibility can be enhanced by setting the reference light and the pulsed light to have different wavelength and diameters.

As described above, in the present exemplary embodiment, the operator can check the light irradiation position while the photoacoustic measurement is in process, by emitting the reference light at the same position as the pulsed light.

Third Exemplary Embodiment

A third exemplary embodiment according to the present invention is described. The present exemplary embodiment has a system configuration that is similar to those of the exemplary embodiments described above, and is described below by mainly focusing on a difference from the exemplary embodiments described above.

An object information obtaining apparatus according to the present exemplary embodiment captures an image of an object being irradiated with pulsed light, and displays, on the input/output unit 106, a position and range respectively corresponding to an actual pulsed light irradiation position and range on the object.

<Processing Flow>

A processing flow according to the present exemplary embodiment is described below with reference to the processing flow illustrated in FIG. 4. An image of the object is captured with the camera 202 after the emission of light in step S405. Thus, the image of the object being irradiated with the pulsed light can be captured. The image captured by the camera 202 may be a still image or a moving image.

Then, the light irradiation position and the light irradiation range on the object can be obtained based on the captured image. For example, an area with pixel values (or a pixel value) each of which is within a predetermined range may be extracted from the image, and the center of the area may be determined as the light irradiation position. An area with pixel values each of which is within a predetermined range is approximately shaped into a circle or ellipse, and the center thereof may be determined as the light irradiation position. Similarly, the light irradiation range may be approximately shaped into a circle or ellipse. In a case the area is extracted, an actually measured position/range may be obtained through a method other than that described above, such as a method for extracting an area with positions where a contrast is large used as a boundary.

Then, the main controller 108 compares the light irradiation position and the light irradiation range obtained from the image with a light irradiation position and a light irradiation range estimated through ray tracing and the like, to determine the amount of deviation of the light irradiation position. When the amount of deviation is equal to or larger than a predetermined value, the main controller 108 forcibly terminates or temporarily stops the measurement processing.

A method for evaluating the amount of deviation is described below.

In one method for evaluating the amount of deviation from the scan path, a distance between light irradiation positions may be used. The irradiation position is determined to have deviated from the scan path set in step S302 in a case the distance between, for example, the center positions of the light irradiation ranges each centered on a different one of adjacent light irradiation positions is equal to or larger than a predetermined threshold. The threshold may be a constant value or may be determined based on the irradiation range calculated in step S403. Alternatively, the threshold may be set by the user. The amount of deviation may also be determined to be equal to or larger than the predetermined value, in a case the distance between the irradiation position calculated in step S403 and the irradiation position set in step S302 is larger than a radius of a larger one of the irradiation range calculated in step S403 and the irradiation range set in step S302.

The amount of deviation from the scan path may be determined based on the size of the light irradiation range. More specifically, the amount of deviation may be determined to be equal to or larger than the predetermined amount, in a case a difference between the irradiation range calculated in step S403 and the irradiation range set in step S302 in size is larger than a threshold. For example, the amount of deviation is determined to be equal to or larger than the predetermined amount when one of the irradiation ranges is 1.5 or greater times larger than the other.

The accuracy of the determination can be enhanced with the plurality of determination methods described above used in combination.

The main controller 108 may count the number of times that the irradiation position calculated in step S403 has deviated from the irradiation position set in step S302, and terminate the photoacoustic measurement in a case the counted number of times exceeds a threshold. The irradiation range may be used for this determination instead of the irradiation position.

The threshold, in the determination related to the number of times the deviated amount has exceeded the threshold, may be set by using the number of acoustic-wave signals constructing each voxel on the reconstructed image. For example, an accuracy of a voxel value calculated by using a small number of photoacoustic signals is low. Thus, a lower limit value of the number of photoacoustic signals used for calculating a voxel value is set. The main controller 108 may forcibly terminate the measurement in a case it is determined that the number of photoacoustic signals that can be obtained is smaller than the lower limit value due to the number the deviation of the irradiation position exceeding the threshold.

A favorable image can be obtained through reconstruction processing based on a position of a generation source of the acoustic waves obtained based on actual light irradiation position and light irradiation range calculated from an image.

An image captured with the camera 202 may be displayed on the input/output unit 106, with a marker indicating the irradiation position displayed on the image in an overlapping manner. The main controller 108 may determine the display position of the marker indicating the irradiation position, based on the positional relationship between the camera 202 and the light emission aperture 103, as well as the shape of the object holding cup 101 and the position of the supporting member 102.

The marker indicating the irradiation position may be displayed only during the measurement processing or while the pulsed light is emitted, and may be continuously displayed so that the operator can check the history of the positions irradiated with the pulsed light.

The color of the marker indicating the irradiation position may be variable in accordance with the color tone of the image captured by the camera 202. In particular, the color of the marker indicating the irradiation position may be set in accordance with a color of a moving image around a position where the marker indicating the irradiation position is displayed. In a case an illuminating unit (not illustrated) that illuminates the object holding cup 101 is additionally provided, the color of the marker indicating the irradiation position may be set in accordance with the color of the illumination. The color of the marker may be automatically set by the main controller 108 or may be set by the operator via the input/output unit 106.

In the present exemplary embodiment, the operator can check the irradiation position and range of the pulsed light while the photoacoustic measurement is in process. Furthermore, a reconstructed image with a high image quality can be expected to be achieved through image reconstruction processing based on the irradiation position and range of the pulsed light.

Fourth Exemplary Embodiment

A fourth exemplary embodiment of the present invention will be described below mainly focusing on a difference from the first exemplary embodiment.

An object information obtaining apparatus according to the present exemplary embodiment includes a measurement light changing unit (not illustrated) that changes a wavelength of pulsed light emitted toward an object. For example, the measurement light changing unit is a spectroscope configured to change the wavelength of pulsed light to be generated in accordance with an instruction from the main controller 108. Alternatively, the object information obtaining apparatus may include a plurality of light sources each generating light of a different wavelength. In a case where the plurality of light sources are provided, a mechanism for switching the light to be emitted as the measurement light toward the object among different types of light with different wavelengths is provided, and such a mechanism may serve as the measurement light changing unit.

The object information obtaining apparatus according to the present exemplary embodiment set an appearance of a marker indicating the light irradiation position in accordance with the wavelength of the pulsed light at each light irradiation position. The term appearance here include a color, size, shape, transparency, blinking pattern, or the like of the marker, and at least one of the listed aspects can be set in accordance with the wavelength of the pulsed light. The appearance of the marker may be set in accordance with the energy amount of the pulsed light obtained in step S408 in the processing flow illustrated in FIG. 4.

<Processing Flow>

FIG. 8A illustrates an example of a display during the measurement processing according to the present exemplary embodiment. In the example illustrated in FIG. 8A, an operator operates a slider 802 to change the wavelength of the pulsed light. In response to the wavelength of the pulsed light being changed with the movement of the slider 802, the resultant wavelength of the pulsed light to be emitted toward an object is displayed on an area 801. An appearance of the marker 803 is set in accordance with the wavelength of the pulsed light that has been set. A record button 804 is a button used for storing, in a storage medium (not illustrated), the light irradiated position and the light irradiation range obtained in step S403 in the processing flow illustrated in FIG. 4, in association with the wavelength of the pulsed light. The stored data may be used for the image reconstruction.

In another embodiment, the wavelength of the pulsed light may be switched while the photoacoustic measurement is being performed along a path. For example, the oxygen saturation in an object may be obtained with a measurement using two wavelengths. This process is described with reference to the flow of the photoacoustic measurement processing illustrated in FIG. 4, and to FIGS. 8B to 8D.

In step S402 in FIG. 4, the main controller 108 controls the position of the supporting member 102, and then in step S405, the main controller 108 irradiates an object with light with a first wavelength. Then, in step S410, the main controller 108 displays a marker corresponding to the light with the first wavelength on the image of the object in an overlapping manner. Then in step S412, in a case where it is determined that the stop button has not been pressed (NO in step S412), the processing returns to step S402, and the measurement light changing unit switches the light to be emitted toward the object to light with a second wavelength. Thus, in step S405, the main controller 108 irradiates the object with the light with the second wavelength. In such a case, in step S410, the main controller 108 displays a marker corresponding to the light with the second wavelength on the image of the object in an overlapping manner. According to the processing, in a case where, for example, two types of pulsed light with different wavelengths are used, the two types of light with different wavelengths are alternately emitted.

Markers may be displayed at substantially the same position on the image, depending on a relationship between an interval of the pulsed light emission and a distance that the probe moves during the interval. In such a case, a single marker may be divided into two areas each having the corresponding wavelength displayed therein, as illustrated in FIG. 8B. The numbers displayed in the marker 813 may be a value of the wavelength set by the operator. Alternatively, in a case where a wavelength measurement unit that measures the wavelength of the pulsed light actually emitted toward the object is provided, a measured value of the wavelength may be displayed. In FIG. 8B, two sliders 812 are provided so that the two types of wavelengths used for the pulsed light can each be changed.

FIG. 8C is a diagram illustrating an example of a display in a case where a measured wavelength of the pulsed light with the second wavelength is different from the set value. Here, for example, a notification is made to the operator in a case where the difference between the set value and the measured value is greater than 15 nm. The main controller 108 displays a message 821 on the image of the object, in response to the wavelength measurement unit notifying the main controller 108 that the measured wavelength is different from the set value by more than a threshold, which is 15 nm in this case. In the present exemplary embodiment, the message 821 is displayed in a form of an icon. Alternatively, a text message may be displayed. The main controller 108 may temporarily stop or terminate the measurement processing in a case where the difference between the measured value and the set value is greater than the threshold.

The position where the marker is displayed is updated as the measurement proceeds. When the measurement ends, the marker is no longer displayed on the image of the object as illustrated in FIG. 8D. In FIG. 8D, a button 831 with an icon different from the icon of the record button 804 is displayed. In response to the operator pressing the button 831, a marker is displayed on the image of the object based on information, such as the light irradiation position, the light irradiation range, and the wavelength, stored during the measurement processing. Here, markers each relating to a different one of a plurality of light irradiation positions may be concurrently displayed, or the position of a marker may be moved to trace the progress of the measurement processing.

In the present exemplary embodiment described above, the operator can not only check an irradiation position of the pulsed light but can also be presented with a larger amount of information in a case where different types of light with different wavelengths are usable as the pulsed light, whereby the usability is enhanced.

Other Exemplary Embodiment

The present invention can be also achieved by the process of supplying a program for implementing one or more functions of the above exemplary embodiments to a system or an apparatus via a network or a storage medium, and causing one or more processors of a computer of the system or the apparatus to read and execute the program. Furthermore, the present invention can be also implemented with a circuit (for example, an application specific integrated circuit (ASIC)) that implements the at least one function.

The exemplary embodiments described above are merely examples, and may be modified without departing from the gist of the present invention. For example, an image obtained by extracting only an outline of the object portion or a monochrome image may be used as the image of the object displayed on the display unit, instead of using the image captured by the camera 202 as it is. In the exemplary embodiments described above, the pulsed light is used as measurement light. The measurement light is not limited to the pulsed light with a rectangular pulse waveform, and may be any light usable for the photoacoustic measurement, such as light with a light intensity trigonometrically changing with respect to time.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

In the exemplary embodiments according to the present invention described above, an operator can check a light irradiation position.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-170585, filed Aug. 31, 2015, and No. 2016-099906, filed May 18, 2016, which are hereby incorporated by reference herein in their entirety.

The invention claimed is:

1. An object information obtaining apparatus configured to obtain information about an interior of an object based on an acoustic wave, the object information obtaining apparatus comprising:
   a memory storing a program; and
   one or more processors which, by executing the program, function as:
   an irradiation unit configured to irradiate the object with measurement light;
   a probe configured to receive the acoustic wave propagating from the object;
   a driving unit configured to move the irradiation unit so that a relative position of the irradiation unit with respect to the object is changed;
   a camera configured to obtain an appearance image of the object by capturing an image of the object;
   an irradiation position estimation unit configured to estimate a plurality of scan patterns including a path related to the measurement light irradiated by the irradiation unit;
   a selection unit configured to select one scan pattern from a plurality of scan patterns; and
   a control unit configured to control a display unit to display the one scan pattern selected by the selection unit superimposed on the appearance image of the object obtained by the camera on the display unit.

2. The object information obtaining apparatus according to claim 1, wherein the irradiation position estimation unit is configured to calculate the irradiation position of the measurement light based on a relative position of the object and the probe.

3. The object information obtaining apparatus according to claim 1,
   wherein the one or more processors which, by executing the program, further function as an irradiation position obtaining unit configured to obtain information about the position, on the object, having been irradiated with the measurement light, as the irradiation position,
   wherein the control unit is configured to calculate a difference between the estimated irradiation position calculated by the irradiation position estimation unit and the irradiation position obtained by the irradiation position obtaining unit.

4. The object information obtaining apparatus according to claim 3, wherein the control unit stops the obtaining of the information about the interior of the object in a case the calculated difference exceeds a predetermined value.

5. The object information obtaining apparatus according to claim 3, wherein the control unit obtains the information about the interior of the object based on the acoustic wave obtained from irradiation position excluding an irradiation position where the calculated difference exceeds a predetermined value.

6. The object information obtaining apparatus according to claim 3, wherein the control unit is configured to control the driving unit based on the difference.

7. The object information obtaining apparatus according to claim 1,
wherein the one or more processors which, by executing the program, further function as a monitoring unit configured to monitor an intensity of the measurement light,
wherein the control unit is configured to set the marker to be different between a case where the monitored intensity of the measurement light is within a predetermined range and a case where the monitored intensity of the measurement light is out of the predetermined range.

8. The object information obtaining apparatus according to claim 7, wherein the control unit is configured to set the marker to be different between a case where the monitored intensity of the measurement light has exceeded an upper limit value of the predetermined range and a case where the monitored intensity of the measurement light has fallen below a lower limit value of the predetermined range.

9. The object information obtaining apparatus according to claim 7, wherein the control unit is configured to set at least one of a size, a shape, and a color of the marker to be different.

10. The object information obtaining apparatus according to claim 1, wherein the control unit is configured to set a display mode for the irradiation position of the measurement light in the image to be different from a display mode at a position not irradiated with the measurement light.

11. The object information obtaining apparatus according to claim 10,
wherein the one or more processors which, by executing the program, further functions as a monitoring unit configured to monitor an intensity of the measurement light,
wherein the control unit is configured to set the display mode for the irradiation position of the measurement light in the image to be different between a case where the monitored intensity of the measurement light is within a predetermined range and a case where the monitored intensity of the measurement light is out of the predetermined range.

12. The object information obtaining apparatus according to claim 1,
wherein the one or more processors which, by executing the program, further function as a reference light irradiation unit configured to irradiate an irradiation position, on the object, with the reference light,
wherein the irradiation position of the measurement light is displayed on the image of the object, by capturing the image of the object with the camera, in a state where the object is irradiated with the reference light.

13. The object information obtaining apparatus according to claim 12, wherein the reference light irradiation unit is configured to irradiate the object with the reference light through a light path that is same as a light path of the measurement light.

14. The object information obtaining apparatus according to claim 12, wherein the reference light is emitted before the measurement light is emitted.

15. The object information obtaining apparatus according to claim 12,
wherein the one or more processors which, by executing the program, further comprising function as an irradiation position obtaining unit configured to obtain information about the irradiation position of the light irradiated on the object,
wherein the control unit is configured to calculate a difference between the irradiation position of the measurement light obtained by using the camera and the irradiation position obtained by the irradiation position obtaining unit.

16. The object information obtaining apparatus according to claim 15, wherein the control unit stops the obtaining of the information about the interior of the object in a case the difference exceeds a predetermined value.

17. The object information obtaining apparatus according to claim 15, wherein the control unit obtains the information about the interior of the object based on the acoustic wave obtained from an irradiation position excluding an irradiation position where the difference exceeds a predetermined value.

18. The object information obtaining apparatus according to claim 15, wherein the control unit is configured to control the driving unit based on the difference.

* * * * *